(12) United States Patent
Omata (10) Patent No.: US 7,648,470 B2
(45) Date of Patent: Jan. 19, 2010

(54) ELASTICITY MEASURING DEVICE FOR BIOLOGICAL TISSUE

(75) Inventor: Sadao Omata, Tokyo (JP)

(73) Assignee: Nihon University, Tokyo (JP)

( * ) Notice: Subject to any disclaimer, the term of this patent is extended or adjusted under 35 U.S.C. 154(b) by 730 days.

(21) Appl. No.: 10/502,240

(22) PCT Filed: Aug. 20, 2002

(86) PCT No.: PCT/JP02/08389

§ 371 (c)(1),
(2), (4) Date: Jul. 21, 2004

(87) PCT Pub. No.: WO03/063698

PCT Pub. Date: Aug. 7, 2003

(65) Prior Publication Data

US 2005/0256387 A1    Nov. 17, 2005

(30) Foreign Application Priority Data

Jan. 29, 2002   (JP) .............................. 2002-020178

(51) Int. Cl.
*A61B 5/103*   (2006.01)
*A61B 5/117*   (2006.01)
(52) U.S. Cl. ........................ 600/591; 600/587
(58) Field of Classification Search ................ 600/595, 600/587, 591
See application file for complete search history.

(56) References Cited

U.S. PATENT DOCUMENTS

| 4,132,224 | A | * | 1/1979 | Randolph | 600/587 |
|---|---|---|---|---|---|
| 4,250,894 | A | * | 2/1981 | Frei et al. | 600/587 |
| 4,432,376 | A | * | 2/1984 | Huszar | 600/587 |
| 4,566,465 | A | * | 1/1986 | Arhan et al. | 128/78 |
| 5,010,892 | A | * | 4/1991 | Colvin et al. | 128/774 |
| 5,054,502 | A | * | 10/1991 | Courage | 600/587 |
| 5,396,887 | A | * | 3/1995 | Imran | 128/642 |
| 5,701,913 | A | * | 12/1997 | McPherson et al. | 600/587 |
| 5,776,081 | A | * | 7/1998 | Kreder | 600/593 |
| 5,860,934 | A | * | 1/1999 | Sarvazyan | 600/587 |
| 5,879,312 | A | * | 3/1999 | Imoto | 600/587 |
| 5,904,658 | A | * | 5/1999 | Niederauer et al. | 600/587 |
| 6,063,044 | A | * | 5/2000 | Leonard et al. | 600/587 |
| 6,215,961 | B1 | * | 4/2001 | Mukai et al. | 396/100 |
| 6,324,344 | B1 | * | 11/2001 | Otsuka | 396/228 |
| 6,351,549 | B1 | * | 2/2002 | Souluer | 382/131 |
| 6,544,199 | B1 | * | 4/2003 | Morris | 600/590 |
| 6,569,108 | B2 | * | 5/2003 | Sarvazyan et al. | 600/587 |
| 6,595,933 | B2 | * | 7/2003 | Sarvazyan et al. | 600/587 |
| 6,659,967 | B1 | * | 12/2003 | Steinberg | 600/587 |
| 6,741,895 | B1 | * | 5/2004 | Gafni et al. | 607/138 |

(Continued)

*Primary Examiner*—Max Hindenburg
*Assistant Examiner*—Jonathan M Foreman
(74) *Attorney, Agent, or Firm*—Wells St. John P.S.

(57) ABSTRACT

We disclose an elasticity-measuring device which can be inserted into a canal part of living body and which is capable of quantitatively measuring the elasticity of the biological tissue of inner side of canal part. The device consists of a probe base (5) and probes (7). The probes (7) are secured to probe base (5) and driven to press onto and return from biological tissue. According to the stress or hardness of the biological tissue measured by sensors on probes (7) and to the deviation between the probes (7) and the probe base (5), we can decide the elasticity of the biological tissue of inner side of canal part quantitatively.

17 Claims, 5 Drawing Sheets

U.S. PATENT DOCUMENTS

| | | | |
|---|---|---|---|
| 6,743,165 B2 * | 6/2004 | Mosel et al. | 600/30 |
| 7,110,124 B2 * | 9/2006 | Jensen et al. | 356/626 |
| 2002/0077568 A1 * | 6/2002 | Haddock | 600/587 |
| 2002/0111586 A1 * | 8/2002 | Mosel et al. | 604/174 |
| 2002/0133093 A1 * | 9/2002 | Mayrose et al. | 600/587 |
| 2004/0114715 A1 * | 6/2004 | Omata | 378/51 |

* cited by examiner

ELASTICITY MEASURING DEVICE FOR BIOLOGICAL TISSUE

CROSS REFERENCE TO RELATED APPLICATION

This application is a 35 U.S.C. §371 of and claims priority to PCT International Application Number PCT/JP02/08389, which was filed 20 Aug. 2002, and was published in English which was based on Japanese Patent Application No. 2002-020178 which was filed 29 Jan. 2002 and the teachings of which are incorporated herein by reference.

BACKGROUND OF THE INVENTION

1. Field of the Invention

The present invention relates to a device for measuring the elasticity of the biological tissue.

2. Description of the Related Art

In the case of women, after the delivery of a child or in accordance with aging, since the muscle suspending the urethra goes slacked and hence its elasticity deteriorates, there is a tendency that incontinence occurs even for slight shock or impact. To cope with this physical problem, an operation for restoring the elasticity of the muscle suspending the urethra is performed in such way that suspension holes are provided in, for example, the pelvis and the muscles around the urethra are suspended with the usage of the suspension holes. To perform an appropriate operation, it is necessary to evaluate an elasticity of the muscles that surround the urethra.

Since the urethra is located near the vagina, the evaluation of elasticity of the muscles surrounding the urethra can be conducted by measuring the elasticity of the biological tissue of an inner surface of a canal part of the vagina. However, since one of the functions of the muscles surrounding the urethra is to enlarge and contract the urethra with an appropriate elasticity, even if the conventional elasticity coefficient or factor for the biological tissue which is represented by the simple ratio of stress and distortion is used, it is impossible to sufficiently evaluate its elasticity characteristics such as viscoelasticity. Since the diameter of the vagina is in the order of 15 mm, it is possible to insert a probe in the canal part thereof. However, in the prior art, there has been no appropriate probe and measuring method for measuring the above elasticity of the muscles that surround the canal part of the vagina and suspend the urethra. Accordingly, the determination of the degree of elasticity deterioration of the muscle around the urethra and the degree of suspending the muscles upwardly using the suspension holes for restoring the elasticity is still made through a diagnosis relied on experiences such as the palpation of the operator's fingers.

SUMMARY OF THE INVENTION

It is, therefore, an object of the present invention to overcome the above problems in the prior art.

It is another object of the present invention to provide an elasticity measuring device for biological tissue which is capable of quantitatively measuring the elasticity of an inner portion of canal part of the biological body.

According to one aspect of the invention, there is provided an elasticity measuring device for being inserted into a canal part of a human body and for measuring elasticity of the inner side of the canal part of the human body, the device comprising:

a probe base for being inserted into the canal part of the human body;

a plurality of probes symmetrically arranged around the probe base, which are located near the inner side of the canal part of the biological tissue when the device is inserted into the canal part and are driven to press onto and return from the biological tissue;

a plurality of resilient arm members each having one end and the other end, the one end supporting thereon corresponding one of the plurality of probes and the other end being firmly fixed to the probe base;

a stress detection sensor provided on each of said probes, for detecting the hysteresis of the stress applied to the biological tissue based on the repulsion from the biological tissue when said probes are driven to press onto and return from the biological tissue; and a deviation detection sensor for detecting the hysteresis of changes in distance of said stress detection sensor with respect to the probe base, wherein the elasticity of the biological tissue is measured based on the hardness and deviation characteristics when the probes are driven to press onto and return from the biological tissue.

According to another aspect of the invention, there is also provided an elasticity measuring device for being inserted into a canal part of a human body and for measuring elasticity of the inner side of the canal part of the biological tissue, the device comprising:

a probe base for being inserted into the canal part of the human body;

a plurality of probes symmetrically arranged around the probe base, which are located near the inner side of the canal part of the biological tissue when the device is inserted into the canal part and are driven to press onto and return from the biological tissue;

a plurality of resilient arm members each having one end and the other end, the one end supporting thereon corresponding one of the plurality of probes and the other end being firmly fixed to the probe base;

a hardness sensor provided on each of the probes, for outputting a signal indicative of hardness of the biological tissue;

a hardness detection means for detecting the hardness of the biological tissue based on the signal from the hardness sensor; and a deviation detection sensor for detecting the deviation magnitude of the hardness sensor with respect to the probe base, wherein the elasticity of the biological tissue is measured based on the hardness and deviation characteristics when the probes are driven to press onto and return from the biological tissue.

In the above elasticity measuring device of the invention, it is preferable that each of the probes comprises a balloon which is hydraulically expandable and contractable and is driven to press onto and return from the biological tissue.

In the above elasticity measuring device of the invention, the hardness sensor comprises a vibration element and a vibration detection sensor. The hardness detection means comprises an input terminal connected to the vibration detection sensor; an output terminal connected to the vibration element; an amplifier having an input coupled to the input terminal; and a phase shift circuit connected between an output terminal of the amplifier and the output terminal, for changing a frequency and making a phase difference zero (0) when there occurs a phase difference between input waveforms applied to the vibration element and output waveforms forwarded from the vibration detection sensor. With the device having the above structure, while a resonant state of the closed loop circuit including the hardness sensor and the biological tissue is maintained, hardness of the biological tissue is preferably detected by the frequency change caused by the change in hardness of the biological tissue.

The elasticity measuring device for the biological tissue of the present invention comprises a probe base for being inserted into the canal part of the human body, and a plurality of probes symmetrically arranged around the probe base, which are located near the inner side of the canal part of the biological tissue when the device is inserted into the canal part and are driven to press onto and return from the biological tissue. The contact pressure against the biological tissue, that is, the stress when the probes are driven to press onto and return from the biological tissue is detected by the stress detection sensor as hysteresis. Also, the deviation magnitude of the stress detection sensor with respect to the probe base, that is, the deviation magnitude of expansion and contraction of the biological tissue is detected by the deviation detection sensor as hysteresis. Based on these hysteresis data, the hysteresis of the stress and deviation magnitude characteristics of the biological tissue is evaluated and, hence, the elasticity of the biological tissue, for example, the viscoelasticity is measured and evaluated experimentally and quantitatively.

The elasticity measuring device for the biological tissue of the present invention comprises a probe base for being inserted into the canal part of the human body, and a plurality of probes symmetrically arranged around the probe base, which are located near the inner side of the canal part of the biological tissue when the device is inserted into the canal part and are driven to press onto and return from the biological tissue. The hardness of the biological tissue when the probes are driven to press onto and return from the biological tissue is detected as hysteresis by the hardness detection means based on the signal of the hardness sensor provided on the probe. Also, the deviation magnitude of the hardness sensor with respect to the probe base, that is, the deviation magnitude of expansion and contraction of the biological tissue is detected by the deviation detection sensor as hysteresis. Based on these hysteresis data, the hysteresis of the hardness and deviation magnitude characteristics of the biological tissue can be evaluated. Since the hardness has an intimate or close relationship to the elasticity coefficient which is a ratio between the stress and distortion, the elasticity of the biological tissue can be quantitatively measured based on analysis of the hysteresis.

The driving of the probes to press onto and return from the biological tissue may well be achieved by the balloon that is hydraulically expanded and contracted, other than the plate spring and motor mechanism.

In one embodiment of the elasticity measuring device of the invention, the device comprises a phase shift circuit which functions to change the frequency and make the phase difference zero (0) when there occurs a phase difference between the input waveforms applied to the vibration element and the output waveforms detected by the vibration detection sensor. With the device having the above construction, while the resonance state of the closed loop circuit including the hardness sensor and the biological tissue is maintained, the hardness of the biological tissue can be quantitatively detected based on the frequency change caused by the change in hardness of the biological tissue, whereby reliability of quantitative evaluation of hardness hysteresis is highly enhanced.

BRIEF DESCRIPTION OF THE DRAWINGS

The above and other objects, features and advantages of the present invention will be apparent from the following description of preferred embodiments of the invention explained with reference to the accompanying drawings, in which.

PREFERRED EMBODIMENTS OF THE INVENTION

Figure 1:
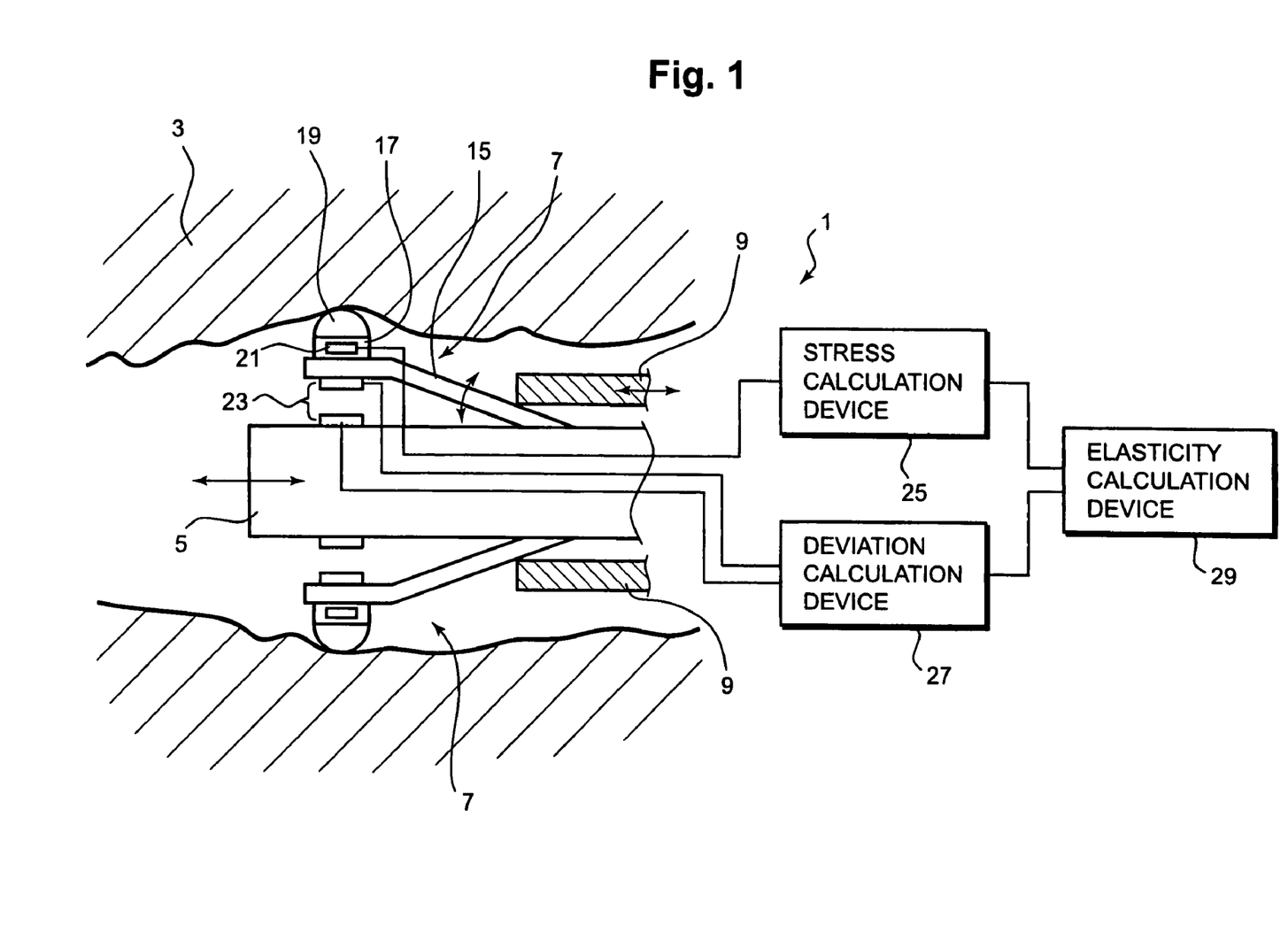
FIG. 1 is a view showing an embodiment of the elasticity measuring device of the invention in the state wherein the device is inserted in the canal part of the human body.

Now, some preferred embodiments of the present invention are explained hereunder with reference to the accompanying drawings. FIG. 1 shows a state in which the elasticity measuring device 1 of the invention is inserted in the canal part of the human body 3. The elasticity measuring device 1 comprises a probe base 5 in the form of an elongated bar having a few mm square or a few mm diameter in section, and a probe 7 secured to the probe base 5, a tip portion of which contacts the inner portion of the canal part 3 of the biological tissue and which is driven to press onto and return from the biological tissue to be measured. To the outer surface of the probe base 5, there is provided a sleeve 9 which has a slightly larger inner diameter than the dimension of the outward form of the probe base 5 and which is movable on the probe base 5 in the elongated axial direction of the probe base 5.

The probe 7 includes a plurality of plate springs 15 which are symmetrically arranged at the outer periphery of the probe base 5, a plurality of stress detection bases 17 correspondingly arranged at the foremost ends of the plate springs 15, and a plurality of contact balls 19 made of plastics in the form of substantial hemisphere. The probe 7 further includes a stress detection sensor 21 adhered to each stress detection base 17. A pair of deviation detection sensors 23 are arranged in such a way that one element is secured to the one side of the plate spring 15 whose side is opposite to the side where the stress detection base 17 is secured and the other element is secured to a surface of the probe base 5 which surface is opposing to the side where the one element is secured. The stress detection sensor 21 and the deviation detection sensors 23 are connected to a stress calculation device 25 and a deviation calculation device 27, respectively, through corresponding signal lines. The outputs of both the stress calculation device 25 and the deviation calculation device 27 are input to an elasticity calculation device 29. The probes 7 are four (4) in number and are arranged around the probe base 5 in a symmetrical relation. The symmetrical relation of the probes 7 is important for the probe base to keep a stationary state when the measuring device is inserted in the canal part of the human body.

Figure 2:
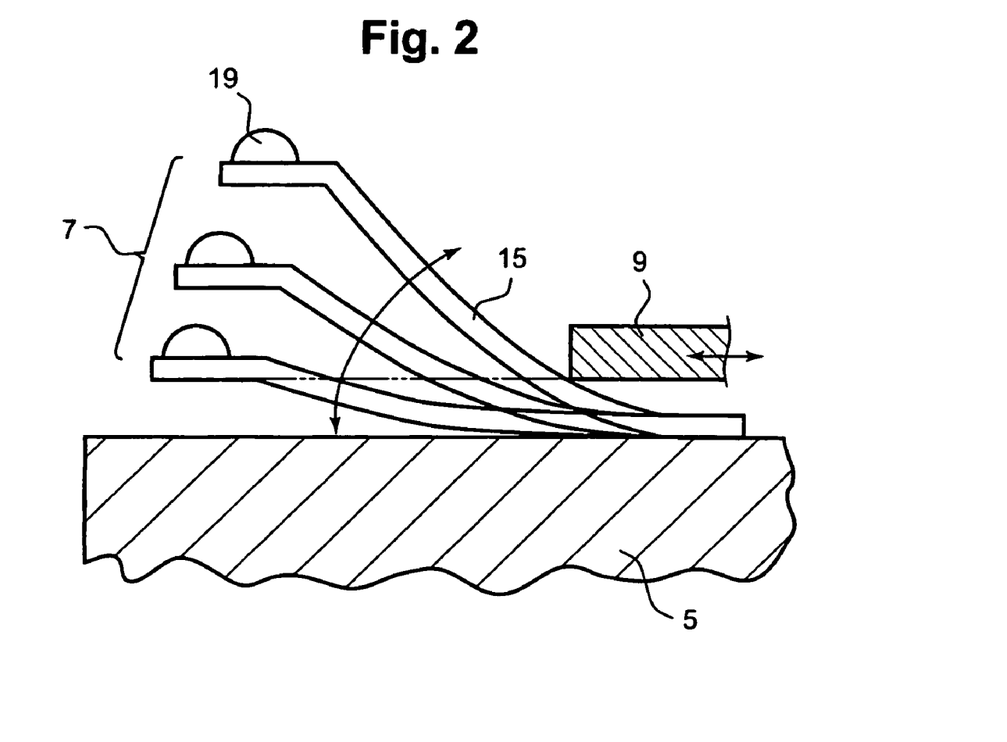
FIG. 2 is a view for explaining the movement of the probe when the probe base and the sleeve arranged around are moved relatively with each other in the longitudinal axial direction.

FIG. 2 is an illustration for explaining the movement of the probe 7 when the probe base 5 and the sleeve 9 arranged around the probe base 5 are moved relatively with each other in the longitudinal axial direction. When the sleeve 9 is moved, for example, leftward in FIG. 2 with respect to the probe base 5, the tubular inner side of the sleeve 9 urges the plate spring 15 of the probe 7, and, in the further advancement of the sleeve 9 in the leftward, it functions to press the plate spring 15 against the probe base side 5. Accordingly, a contact ball 19 arranged at the foremost end of the probe 7 moves downward in the drawings as the sleeve 9 moves in the leftward, whereas it moves upward as the sleeve 9 moves in the rightward. In this way, the contact ball 19 at the foremost end of the probe 7 can be driven to press onto and return from the biological tissue by the simple relative movement between the sleeve 9 and the probe base 5. The relative movement between the sleeve 9 and the probe base 5 can be achieved by such small motor as a micro-motor (not shown in the drawings). Further, in the case of a simple measurement, such relative movement between the sleeve 9 and the probe base 5 can be performed manually by the operator's hands and fingers.

With the leftward movement of the sleeve 9, the probe 7 including the contact ball 19 can be entirely accommodated within the sleeve 9. In this case, since the elasticity measuring device 1 for the biological tissue can be inserted to a desired portion of the biological tissue to be measured in the state in which the probe 7 having the complicated structure is fully accommodated within the sleeve 9 being kept, the insertion of the device can be effected smoothly. Thereafter, at the desired measuring position after the insertion, the four probes 7 can be opened and closed in an umbrella fashion by the movement of the sleeve 9. The number of the probes is not limited to four as in the above embodiment, and it may well be any appropriate number, for example, one, two, three, six and so on.

Figure 3:
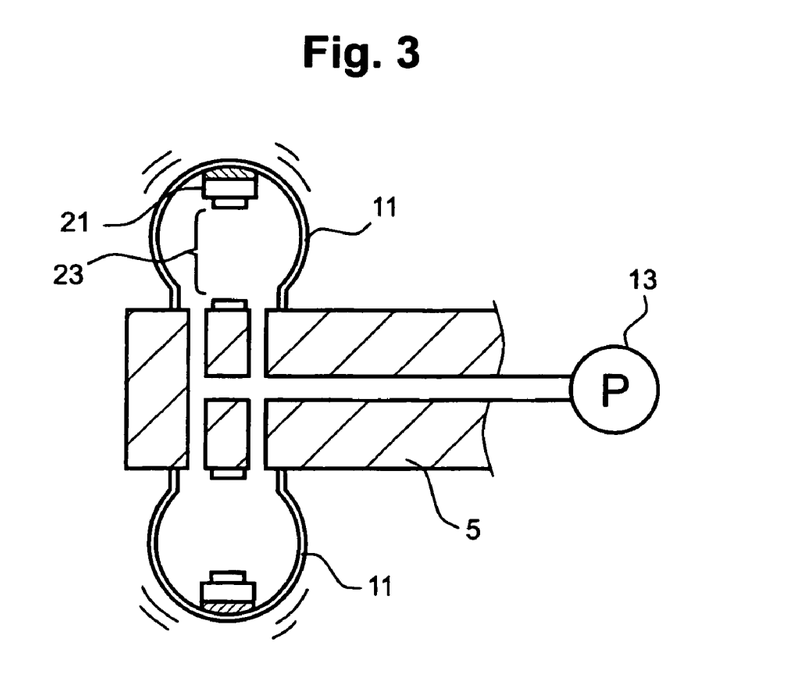
FIG. 3 is a view showing another embodiment of the elasticity measuring device of the invention in which balloons are secured to the probe base as the probes.

As the structure of the probe which is driven to press onto and return from the biological tissue, other than the above explained plate spring structure, a balloon which is hydraulically expandable and contractable may well be adopted. FIG. 3 shows such embodiment in which a plurality of balloons 11 are secured to the probe base 5. The balloon 11 is hydraulically communicated with a pump 13 and is driven to press onto and return from the biological tissue by the control of the output pressure of the pump 13.

Figure 4:
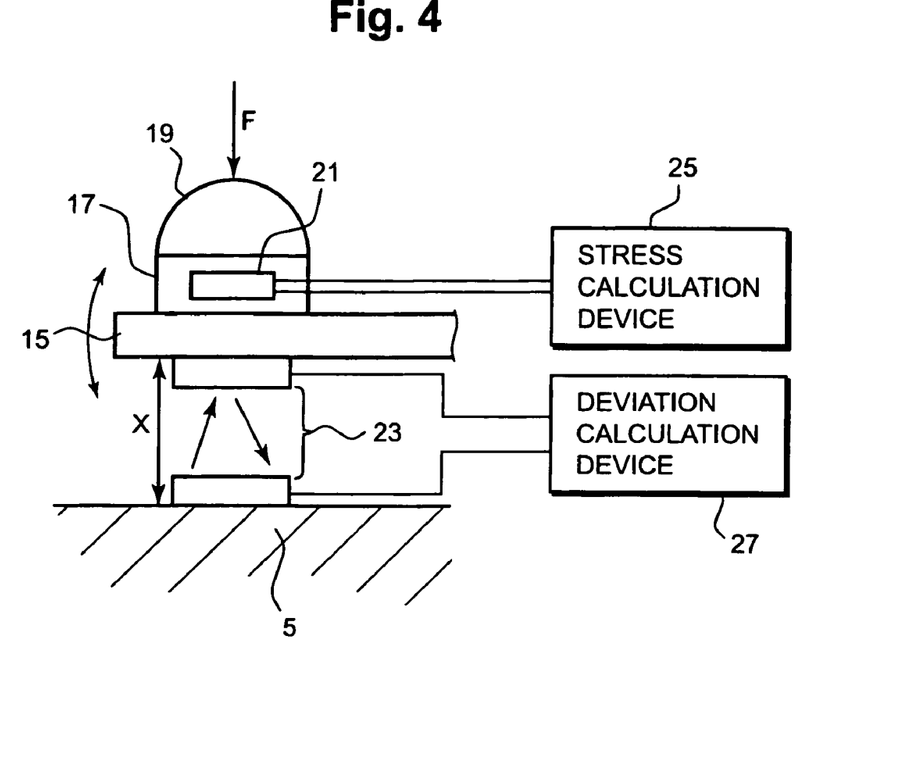
FIG. 4 is a view showing the details of the foremost end of the probe of the elasticity measuring device of the invention.

FIG. 4 shows in detail the foremost portion of the probe 7 shown in FIG. 1. To the foremost end of the plate spring 15, there is adhered the hemispherical contact ball 19 made of plastics having the stress detection base 17 on the surface thereof opposing to the biological tissue. The stress detection sensor 21 is arranged within the stress detection base 17. The stress detection sensor 21 is a distortion gauge and is firmly adhered to the stress detection base 17 using an adhesive agent. To the side of the plate spring 15 whose side is an opposite side where the reaction detection base 17 is arranged, there is provided a light receiving element. A light emitting element opposing to the light receiving element is provided on the surface of the probe base 5. The above pair of light emitting and light receiving elements constitutes the deviation detection sensor 23. The stress detection sensor 21 and the deviation detection sensor 23 are connected to the stress calculation device 25 and the deviation calculation device 27, respectively, by the respective signal lines. Though the stress detection base 17 and the contact ball 19 are made of the same material, they may well be made of different materials and may well be in a stacked configuration. The deviation detection sensor, which is constituted by a pair of the light emitting and light receiving element in the illustrated embodiment, may well be constituted by a combination of a magnet and a magnetic sensor, for example, or other small contactless sensor.

Next, actual operation of the device having the above structure will be explained hereunder. The probe base 5 with the four probes 7 arranged symmetrically around the probe base 5 being closed in an umbrella fashion is inserted into the canal part of the human body, namely, the vagina of the patient. Then, at the position where the elasticity of the biological tissue is to be measured, the probes 7 are opened by gradually moving the sleeve 9 relative to the probe base 5 in the rightward in FIG. 1. By so doing, the contact ball 19 moves toward the biological tissue side and urges to press against the biological tissue of the canal part. Thereafter, the sleeve 9 is gradually moved or returned in the leftward with respect to the probe base 5 so that the probes 7 are folded. The stress F from the biological tissue at every moment when the probes drive to press onto and return from the biological tissue is detected by a pressure detection sensor 21 which is arranged on the stress detection base 17 to which the contact ball 19 is also provided. In the case where the pressure detection sensor is a distortion gauge, the detected result as the variations in resistance is forwarded to the stress calculation device 25 by a signal line and converted to the corresponding stress after the necessary calculation process.

The change in distance of the contact ball 19 with respect to the probe base 5, that is, the relative variation occurring when the contact ball 19 is driven to press onto and return from the biological tissue 3 is detected by the deviation detection sensor 23. Specifically, as the distance of the contact ball 19 with respect to the probe base 5 changes, the distance between the paired light emitting and receiving elements 23 changes accordingly. The change in the amount of received light corresponding to the change in the above distance is forwarded to the deviation amount calculation device 27 through the signal line and the magnitude of deviation is obtained thereat after the necessary calculation process.

Figure 5:
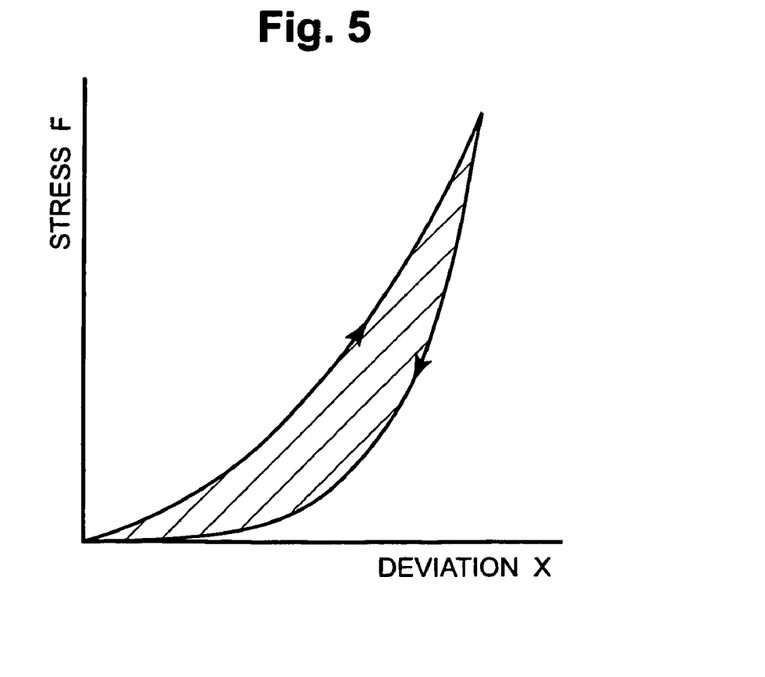
FIG. 5 is a graph showing the changes in the stress F (vertical line) and the deviation magnitude X (horizontal line) when the probes of the device of the invention are driven to press onto and return from the desired measuring portion.

In this way, the stress F and the corresponding deviation magnitude X are obtained under the condition where the probes are driven to press onto and return from the biological tissue. The probe base 5 is positioned stationary at the desired measuring point of the biological tissue after the insertion and, then, in the case of FIG. 1 illustration, the sleeve 9 is gradually moved in the rightward with respect to the probe base 5 and then gradually moved to the leftward again. By so doing, the contact ball 19 is first pressed against the biological tissue and then returned therefrom. Specifically, by making the stress F and the changes in the deviation magnitude X have correlation, it is possible to analyze the hysteresis of the elasticity of the biological tissue. FIG. 5 is an exemplary graph which shows the changes in the stress F and the deviation magnitude X of the biological tissue when the probe 7 is driven to press onto and return from the biological tissue at the desired measuring point. The vertical line denotes the stress F and the horizontal line denotes the deviation magnitude X. As shown in FIG. 5, as a hysteresis curve of the elasticity of the biological tissue can be obtained, it has been made possible to measure and evaluate the elasticity of the biological tissue experimentally and quantitatively. The viscoelasticity of the biological tissue can be quantitatively evaluated by, for example, the size of area surrounded by the obtained hysteresis curve.

Figure 6:
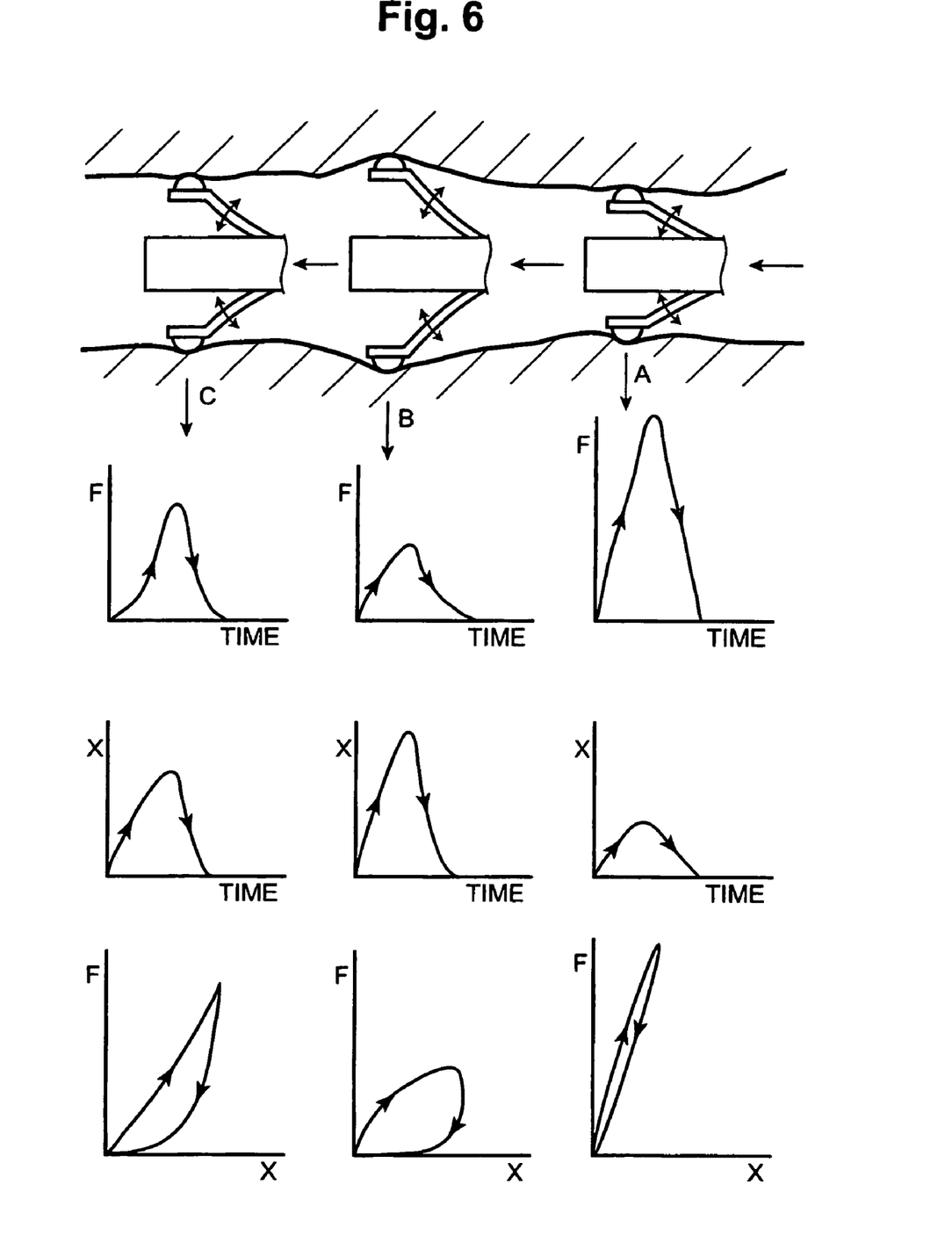
FIG. 6 is graphs showing exemplary measured elasticity characteristics when the measurements are conducted at different three points of the canal part of the human body.

FIG. 6 shows exemplary graphs of the elasticity when the measurements are conducted at different three points of the canal part of the human body. At the three points A, B and C where the depth of the insertion of the probe base 5 into the canal part of the human body are different from one another, the probes 7 are driven to press onto and return from the inner side of the canal part of the human body, the hysteresis characteristics of the stress F and the deviation magnitude X at that time are obtained and illustrated for the purpose of comparison with the stress F taken as the vertical line and the deviation magnitude X taken as the horizontal line. For example, comparing the hysteresis characteristics at the point A with those at the point B or C, since the area surrounded by the hysteresis curve at the point A is smaller than the area at the point B or C, it can be quantitatively evaluated that the elasticity at the point A is greater than the elasticity at the point B or C.

As has been explained hereinabove, it has been made possible to measure and evaluate the elasticity of the biological tissue by evaluating or analyzing the hysteresis characteristics between the stress and the distortion based on the measurements of the stress and the distortion of the biological tissue. On the other hand, since the hardness has an intimate or close relationship to the elasticity coefficient which is a ratio between the stress and the distortion, it is also possible to quantitatively measure and evaluate the elasticity of the biological tissue based on the hysteresis of the hardness.

Figure 7:
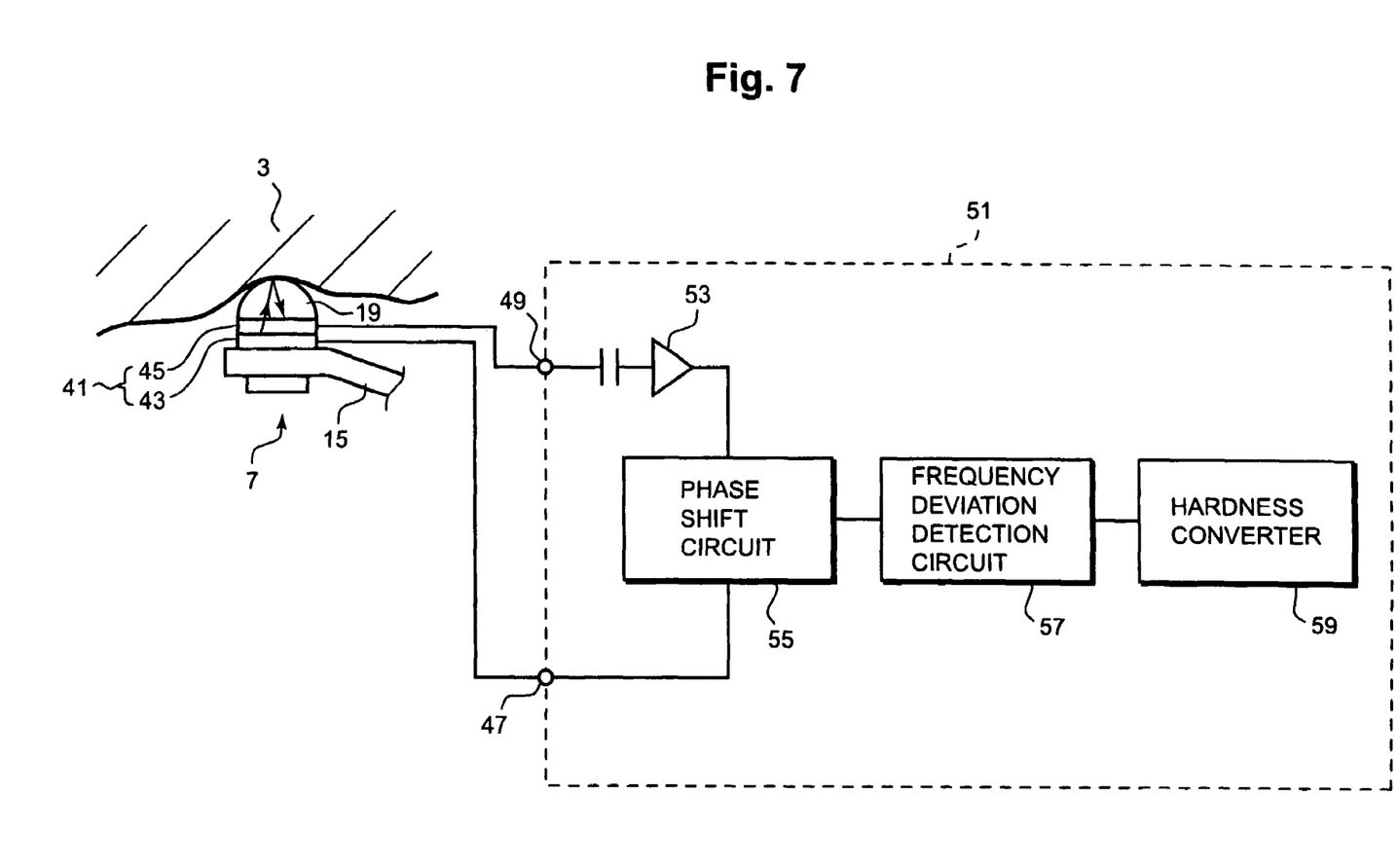
FIG. 7 is a view showing a still further embodiment of the elasticity measuring device of the invention using a hardness detection device.

FIG. 7 is a block diagram showing another embodiment of the elasticity measuring device for the biological tissue according to the invention, in which the hardness of the biological tissue is measured. A hardness sensing device 41 includes a vibration element 43 and a vibration detector 45 at the foremost end portion of the probe 7. The vibration element 43 and the vibration detector 45 are connected to an output terminal 47 and an input terminal 49, respectively, of a hardness detection means 51. The hardness detection means 51 includes an amplifier 53 whose input node is coupled to the input terminal 49, and a phase shift circuit 55 connected between an output node of the amplifier 53 and the output terminal 47. The phase shift circuit 55 operates to change the frequency and make the phase difference zero (0) when there occurs a phase difference between the input waveforms applied to the vibration element 43 and the output waveforms forwarded from the vibration detector 45. The detail of such phase shift circuit having the above functions is disclosed in the Japanese Patent Application Kokai-Publication No. Hei 9-145691 which should be incorporated by reference in this application.

In the device having the above construction, while the resonance state of the closed loop circuit including the hardness sensor 41 and the biological tissue is maintained, the change in frequency caused by the change in hardness of the biological tissue is detected by the frequency deviation detection circuit 57 and, then, the detected change is converted to the value of hardness by the hardness converter 59. In this way, with the probe being driven to press onto and return from the biological tissue, hysteresis characteristics in relation to the hardness of the biological tissue can be quantitatively measured and obtained.

With the elasticity measuring device for the biological tissue according to the present invention, the elasticity of the measured biological tissue can be quantitatively measured by simply inserting the canal part of the human body with additional simple operation being followed.

While the invention has been described in its preferred embodiments, it is to be understood that the words which have been used are words of description rather than limitation and that changes within the purview of the appended claims may be made without departing from the true scope of the invention as defined by the claims.

The invention claimed is:

1. An elasticity measuring device for being inserted into a canal part of a human body and for measuring elasticity of the inner side of the canal part of the human body, said device comprising:
   a probe base for being inserted into the canal part of the human body;
   a probe arranged around said probe base, which is located near the inner side of the canal part of the human body when the device is inserted into the canal part and is driven to press onto and return from the biological tissue;
   a resilient arm member having one end and an other end, said one end supporting said probe thereon and said other end being firmly fixed to said probe base, said resilient arm member comprising a plurality of spring members, said probe comprising a plurality of probes being symmetrically arranged around said probe base through corresponding spring members;
   a stress detection sensor provided on at least one of the plurality of probes, for detecting hysteresis of the stress applied to the biological tissue based on the repulsion from the biological tissue when said at least one of the plurality of probes is driven to press onto and return from the biological tissue; and
   a deviation detection sensor for detecting the hysteresis of changes in distance of said stress detection sensor with respect to said probe base;
   wherein the elasticity of the biological tissue is measured based on the stress and deviation magnitude characteristics when the at least one of the plurality of probes is driven to press onto and return from the biological tissue.

2. An elasticity measuring device for biological tissue according to claim 1, in which said deviation detection sensor comprises a pair of light emitting element and light receiving element, said light emitting element being secured on a surface of said probe base and said light receiving element being secured on at least one of the plurality of the spring members so as to oppose to each other.

3. An elasticity measuring device for biological tissue according to claim 1, in which said stress detection sensor comprises a distortion gauge.

4. The device of claim 1 wherein the probe base comprises an elongated bar.

5. The device of claim 1 wherein the probe base comprises an outer surface, and wherein the plurality of the probes is configured to move substantially perpendicularly to the outer surface of the probe base.

6. The device of claim 1 wherein each of the plurality of the springs members comprises a plate spring.

7. The device of claim 1 further comprising a sleeve, wherein the sleeve and the probe base are configured to move relative each other in a longitudinally axial direction, and wherein the relative movement of the sleeve and the probe base moves the plurality of the probes in substantially a perpendicular direction relative the longitudinally axial direction.

8. The device of claim 1 wherein the probe base comprises an elongated structure that extends along a longitudinal axis, and wherein the plurality of the probes is configured to move substantially perpendicularly to the longitudinal axis.

9. The device of claim 1 wherein the probe base comprises a square cross section.

10. The device of claim 1 wherein the plurality of the probes is in a fixed relation relative the plurality of the springs members of the resilient arm member.

11. The device of claim 1 wherein the plurality of the probes is affixed to respective ones of the plurality of the springs members of the resilient arm member.

12. The device of claim 1 wherein the stress detection sensor is affixed to at least one of the plurality of the spring members of the resilient arm member.

13. The device of claim 1 wherein the deviation detection sensor is affixed to at least one of the plurality of the spring members of the resilient arm member.

14. The device of claim 1 wherein an entirety of the structure of each of the plurality of the spring members of the resilient arm member comprises a substantially solid structure.

15. The device of claim 1 wherein an entirety of the structure of each of the plurality of the spring members of the resilient arm member comprises a single structure, and the single structure comprising resiliency.

16. An elasticity measuring device for being inserted into a canal part of a human body and for measuring elasticity of the inner side of the canal part of the human body, said device comprising:
- a probe base for being inserted into the canal part of the human body;
- at least one probe arranged around said probe base, which is located near the inner side of the canal part of the human body when the device is inserted into the canal part and is driven to press onto and return from the biological tissue;
- a resilient arm member having one end and an other end, said one end supporting said at least one probe thereon and said other end being firmly fixed to said probe base;
- a stress detection sensor provided on said probe, for detecting hysteresis of the stress applied to the biological tissue based on the repulsion from the biological tissue when said probe is driven to press onto and return from the biological tissue;
- a deviation detection sensor for detecting the hysteresis of changes in distance of said stress detection sensor with respect to said probe base;
- wherein the elasticity of the biological tissue is measured based on the stress and deviation magnitude characteristics when the probe is driven to press onto and return from the biological tissue; and
- wherein the probe base comprises an elongated structure that extends along a longitudinal axis, and wherein the at least one probe is configured to move substantially perpendicularly to the longitudinal axis.

17. An elasticity measuring device for being inserted into a canal part of a human body and for measuring elasticity of the inner side of the canal part of the human body, said device comprising:
- a probe base for being inserted into the canal part of the human body;
- at least one probe arranged around said probe base, which is located near the inner side of the canal part of the human body when the device is inserted into the canal part and is driven to press onto and return from the biological tissue;
- a resilient arm member having one end and an other end, said one end supporting said at least one probe thereon and said other end being firmly fixed to said probe base;
- a stress detection sensor provided on said probe, for detecting hysteresis of the stress applied to the biological tissue based on the repulsion from the biological tissue when said probe is driven to press onto and return from the biological tissue;
- a deviation detection sensor for detecting the hysteresis of changes in distance of said stress detection sensor with respect to said probe base;
- wherein the elasticity of the biological tissue is measured based on the stress and deviation magnitude characteristics when the probe is driven to press onto and return from the biological tissue; and
- wherein the deviation detection sensor is affixed to the resilient arm member.

* * * * *